United States Patent [19]

Takahashi

[11] 4,178,810

[45] Dec. 18, 1979

[54] APPARATUS FOR MANIPULATING A MEDICAL INSTRUMENT

[76] Inventor: Nagashige Takahashi, Tokiwadai Green Haitsu 602, No. 28-10, Tokiwadai 3-chome, Itabashi-ku, Tokyo, Japan

[21] Appl. No.: 823,074

[22] Filed: Aug. 9, 1977

[30] Foreign Application Priority Data

Aug. 12, 1976 [JP] Japan .................. 51/107796

[51] Int. Cl.$^2$ .................. F16C 1/10; A61B 5/00; A61B 17/00; F16B 7/10
[52] U.S. Cl. .................. 74/501 R; 403/166; 128/751; 128/303 R
[58] Field of Search .................. 74/501.5, 501 R; 403/166, 361; 128/305, 328, 2 B, 3 H, 2 M, 348, DIG. 9, 2.05 R, 307, 303 R

[56] References Cited

U.S. PATENT DOCUMENTS

| 932,381 | 8/1909 | Folmer | 74/501.5 |
|---|---|---|---|
| 1,331,311 | 2/1920 | Au | 74/501.5 |
| 1,406,768 | 2/1922 | Slater | 403/166 |
| 2,421,354 | 5/1947 | Reiter | 128/303 R |
| 2,437,014 | 3/1948 | Arnesen et al. | 128/303 R |
| 2,905,178 | 9/1959 | Hilzinger | 128/348 |
| 2,957,354 | 10/1960 | Morrow | 74/501.5 |
| 3,016,761 | 1/1962 | Wrighton et al. | 74/501.5 |
| 3,186,745 | 6/1965 | Lyles | 403/361 |
| 3,552,384 | 1/1971 | Pierie | 128/348 |

Primary Examiner—Dalton L. Truluck
Assistant Examiner—C. W. Shedd
Attorney, Agent, or Firm—Sughrue, Rothwell, Mion, Zinn and Macpeak

[57] ABSTRACT

The manipulator end of an endoscopic tissue sampling instrument, such as a forceps, comprises a plunger 4 slidably disposed within a slotted support tube 3 and movable via a finger sleeve 6 surrounding the tube and coupled to the plunger. A control wire 1 extends through an inner coil 10 and a surrounding outer coil 8; the adjoining ends of the coils within the support tube are brazed or welded together at 13, and the other end of the outer coil is secured to the end of the support tube by set screws 9. An end stop 2 is attached to the end of the control wire and is normally seated against one end of a cavity 5 within the plunger by a spring 7. If excessive tension is exerted on the control wire in manipulating the instrument the outer coil 8 expands in a spring-like manner to prevent any breakage or damage; if excessive compression is exerted the end stop spring yields to allow the stop to unseat and move within the cavity.

4 Claims, 1 Drawing Figure

U.S. Patent  Dec. 18, 1979  4,178,810
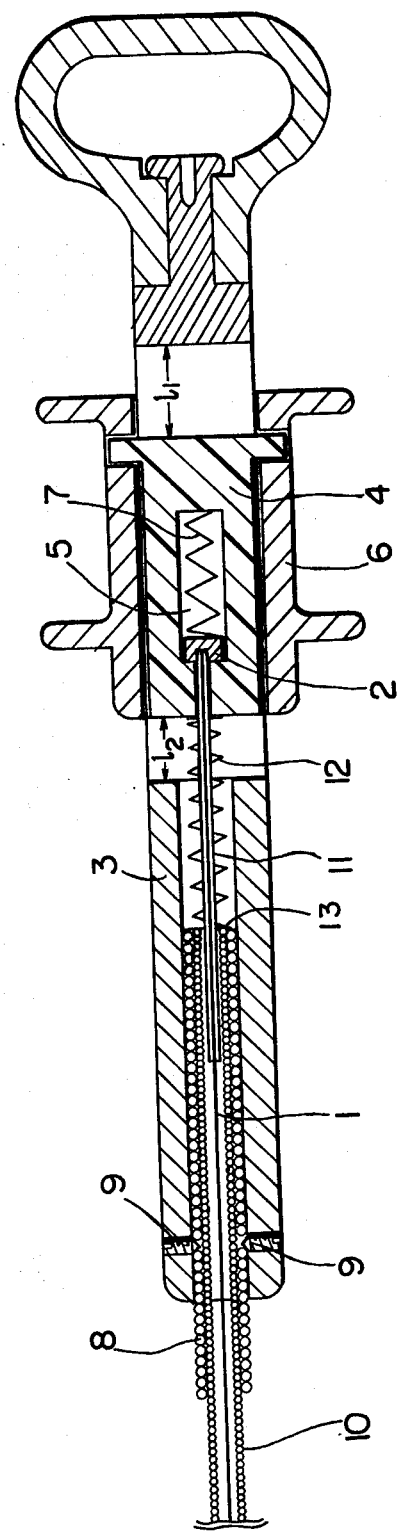

APPARATUS FOR MANIPULATING A MEDICAL INSTRUMENT

BACKGROUND OF THE INVENTION

This invention relates to a tissue sampling instrument, such as a forceps, employed in connection with a flexible fiberscope, and more particularly to such an instrument constructed to prevent the flexible control wire connected between the sampling device and the manipulating section from breaking and the forceps cup section at the end of the sampling device from being damaged, as by the application of violent or excessive operating force.

In the prior art tissue sampling instruments the operator grips the manipulating knob while simultaneously observing the internal body part or organ to be examined through a fiberscope or the like in order to properly direct or aim the instrument at the desired tissue or cells. In such a procedure the operator's attention is primarily occupied in observing the area under examination and in guiding the end of the instrument to the desired location, and he is thus liable to apply excessive force in manipulating or opening and closing the sampling device, which may lead to the breakage of the control wire or damage to the forceps sampling cup.

Further, in view of the curvature of the insertion path leading to the area to be examined the control wire must be relatively long in order to reach remote areas, and its length often changes with time and use. It is thus not practical to provide a stop mechanism to limit the movement of the operating knob to within a certain range to prevent wire breakage or damage.

SUMMARY OF THE INVENTION

Briefly, and in accordance with the present invention, the manipulator end of an endoscopic tissue sampling instrument, such as a forceps, comprises a plunger slidably disposed within a slotted support tube and movable via a finger sleeve surrounding the tube and coupled to the plunger. A control wire extends through an inner coil and a surrounding outer coil; the adjoining ends of the coils within the support tube are brazed or welded together, and the other end of the outer coil is secured to the end of the support tube by set screws. An end stop is attached to the end of the control wire and is normally seated against one end of a cavity within the plunger by a spring. If excessive tension is exerted on the control wire in manipulating the instrument the outer coil expands in a spring-like manner to prevent any breakage or damage; if excessive compression is exerted the end stop spring yields to allow the stop to unseat and move within the cavity.

BRIEF DESCRIPTION OF THE DRAWING

The single FIGURE in the accompanying drawing shows a longitudinal sectional view of a tissue sampling instrument constructed in accordance with this invention.

DETAILED DESCRIPTION OF THE PREFERRED EMBODIMENT

Referring to the accompanying drawing, an end stop 2 is fixedly secured to one end of a control wire 1 whose other end is connected to the cup operating mechanism of a conventional tissue sampling device (not shown). A plunger 4 is slidably disposed in grooves in the opposite sides of a support tube 3 for movement together with a surrounding outer finger sleeve 6. The plunger 4 has an internal cavity 5 in which the end stop 2 is engaged. A spring 7 urges the end stop against one end of the cavity 5 so as to bias the control wire out of the plunger. The elastic force of the spring 7 is selected to be stronger than the force required to open the forceps cup but weaker than the force which would damage the cup operating mechanism or break the control wire.

A relatively large diameter flexible outer coil 8 is secured at one end to the support tube 3 with set screws 9. The control wire 1 and a relatively small diameter flexible inner coil 10 surrounding the control wire are inserted through the outer coil 8 into the support tube. The adjoining inner ends of the flexible coils 8 and 10 are secured together at 13 by brazing or the like. The end length of the control wire is covered by a guide tube 11 connected to the end stop 2. A forceps cup closure spring 12 is disposed around the guide tube between the joined ends of the coils 8, 10 and the plunger 4. The stroke length over which the plunger can move with respect to the support tube 3 to close the forceps cup is designated $l_1$, while $l_2$ designates the stroke length over which the plunger can move to open the cup.

The plunger 4 and finger sleeve 6 are normally positioned as shown in the drawing. In this condition the control wire 1 is under sufficient tension from the spring 12 to hold the forceps cup "moderately" closed, whereby the insertion of the instrument into the patient can be accomplished with ease and safety. To obtain a tissue sample or specimen the sleeve 6, and with it the plunger 4, is moved to the left in the drawing against the force of the spring 12. Accordingly, owing to the force of the spring 7 holding the end stop 2 against its seat in the cavity 5, the control wire 1 is also moved to the left out of the inner coil 10 to operate the cup opening mechanism. If, after the cup has been fully opened, the sleeve 6 and plunger 4 are further depressed, the spring 7 will yield and be compressed to thereby prevent damage to the cup mechanism. After the full stroke distance $l_2$ has been traversed, the plunger is stopped by its abutment against the end of the support tube 3.

To close the forceps cup to sever and extract the desired tissue sample, the finger sleeve 6 and plunger 4 are moved to the right in the drawing whereby the end stop 2 seats at its one end of the cavity 5 and draws the control wire 1 through the inner coil 10. If excessive or further force is exerted after the forceps cup has been fully closed, the end of the inner coil 10, through which the control wire extends, is pushed to the right in the drawing, which expands the larger diameter outer coil 8 in a spring-like manner. Thus, the flexible outer coil 8 serves the dual functions of reinforcing the end of the inner coil 10 where it exits the support tube 3 to prevent breakage and absorbing excessive tension in the base section of the control wire 1. The plunger 4 is of course stopped when it has moved over the full stroke distance $l_1$ and abuts the thumb hole end of the support tube.

What is claimed is:

1. An apparatus for manipulating a medical instrument, such as a tissue sampling forceps, via a control wire slidably disposed within a flexible guide coil, comprising a flexible guide coil and a control wire slidably disposed within said guide coil, said apparatus further comprising:

(a) a hollow, elongated support tube, (b) a plunger having an elongated cavity therein and being slidably disposed in the support tube, (c) means coupled to the plunger for moving same within the support tube, (d) a flexible expansion coil concentrically surrounding the guide coil within the support tube, one end of the expansion coil being secured to the support tube and the other end of the expansion coil being secured to the end of the guide coil, (e) a stop member secured to the end of the control wire and slidably disposed within the cavity, and (f) a spring disposed within the cavity for biasing the stop member against one end thereof, whereby the expansion coil yieldingly extends in response to excessive tension exerted on the control wire and the spring yieldingly compresses in response to excessive compression exerted on the control wire, thereby preventing breakage of or damage to the control wire and/or a medical instrument controlled thereby.

2. An apparatus as defined in claim 1, wherein the support tube has at least one axial slot in its side, the plunger includes a projection extending outwardly through the slot, and the means for moving the plunger comprises a sleeve concentrically surrounding the support tube and engaged with the projection.

3. An apparatus as defined in claims 1 wherein the expansion coil extends out beyond the end of the support tube to protect the guide coil.

4. An apparatus as defined in claim 1, further comprising a second spring disposed between the plunger and the secured ends of the guide and expansion coils for biasing the plunger away from the coils.

* * * * *